(12) United States Patent
Kerver

(10) Patent No.: US 6,223,081 B1
(45) Date of Patent: Apr. 24, 2001

(54) IMPLANTABLE STIMULUS SYSTEM HAVING STIMULUS GENERATOR WITH PRESSURE SENSOR AND COMMON LEAD FOR TRANSMITTING STIMULUS PULSES TO A BODY LOCATION AND PRESSURE SIGNALS FROM THE BODY LOCATION TO THE STIMULUS GENERATOR

(75) Inventor: Harry B. A. Kerver, Duiven (NL)

(73) Assignee: Medtronic, Inc., Minneapolis, MN (US)

( * ) Notice: Subject to any disclaimer, the term of this patent is extended or adjusted under 35 U.S.C. 154(b) by 459 days.

(21) Appl. No.: 08/625,714

(22) Filed: Mar. 28, 1996

(51) Int. Cl.$^7$ ..................................................... A61N 1/18
(52) U.S. Cl. ............................ 607/17; 607/18; 607/19; 607/23; 607/36; 607/37
(58) Field of Search .................... 607/17–19, 23, 607/36, 37

(56) References Cited

U.S. PATENT DOCUMENTS

| | | | |
|---|---|---|---|
| 4,407,296 | 10/1983 | Anderson | 128/675 |
| 4,763,646 | 8/1988 | Lekholm | 607/14 |
| 4,899,751 | * 2/1990 | Cohen | 607/23 |
| 5,188,078 | 2/1993 | Tamaki | 123/403 |
| 5,312,441 | 5/1994 | Mader et al. | 607/5 |
| 5,320,643 | * 6/1994 | Roline et al. | 607/28 |
| 5,342,406 | 8/1994 | Thompson | 607/22 |
| 5,353,800 | 10/1994 | Pohndorf et al. | 128/673 |
| 5,556,421 | * 9/1996 | Prutchi et al. | 607/36 |

* cited by examiner

Primary Examiner—Carl H. Layno
(74) Attorney, Agent, or Firm—Thomas F. Woods; Michael J. Jaro; Harold Patton

(57) ABSTRACT

A medical device system such as a pacemaker system is provided wherein pressure signals representative of a patient's cardiac movements are transmitted through a pacing lead to the pacemaker, where they are sensed and utilized for control of pacemaker operation. In a preferred embodiment, the invention utilizes a standard pacing lead, which may already be in place within the patient, the lead having a lumen through which relative pressure signals are transmitted from the patient's heart to the proximal end of the lead. The proximal end of the lead is connected to a pressure sensor, mounted either in the pacemaker header portion or within the hermetically sealed pacemaker can. The sensor signals are coupled to appropriate processing circuitry and are used for control of one or more pacing parameters, such as pacing rate. In a first embodiment, the pressure sensor is mounted within the pacemaker header portion, and the electrical sensor signals are connected through an electrical feed-through to the interior of the pacemaker can. In a second embodiment, the sensor signals are passed through a capillary feed-through from the proximal end of the lead which is secured in the header portion, to the interior of the pacemaker can where the pressure sensor is mounted; the capillary feed-through may also conduct sensed heart signals from the proximal end of the lead to within the pacemaker.

15 Claims, 2 Drawing Sheets

IMPLANTABLE STIMULUS SYSTEM HAVING STIMULUS GENERATOR WITH PRESSURE SENSOR AND COMMON LEAD FOR TRANSMITTING STIMULUS PULSES TO A BODY LOCATION AND PRESSURE SIGNALS FROM THE BODY LOCATION TO THE STIMULUS GENERATOR

FIELD OF THE INVENTION

This invention relates to the field of implantable medical devices and, more particularly, to a pacemaker system having a pacemaker which contains a pressure sensor in combination with a pacing lead which connects stimulus pulses to the patient's heart and which is operatively connected to the pacemaker so as to transmit cardiac pressure signals to the pressure sensor.

BACKGROUND OF THE INVENTION

In the area of implantable medical devices, there has been a substantial effort to develop sensors for obtaining information from a body organ such as the heart, or relating to a body function such as respiration. For these purposes, catheters and leads have been widely used with medical devices, both external and implantable, including pacemakers, cardioverter/defibrillators, drug dispensers, cardiac monitors, and a variety of different types of stimulators. The common system arrangement is to have one or more catheters, or leads which interconnect the device with the body organ or body location. The terms catheter and lead are used interchangeably here; as used in this specification, either a lead or catheter connects the device to the body location so as to transmit electrical signals between its distal end and the device, and/or pressure or other signals from the body location to the device. A pacing lead, for example, may include one or more electrodes at about its distal end, and a conductor running the length of the lead to transmit stimulus pulses to the heart and conduct heart signals back to the pacemaker. It is also known to have sensors incorporated into the lead for sensing parameters for operational and diagnostic use, with additional conductors connecting the sensor signals back to the proximal end of the lead/catheter, for connection to the pacemaker or other device. In addition to sensing cardiac electrical activity, sensors are used for sensing, eg, blood pressure waves, acoustic waves, respiratory sounds, etc. Thus, for a wide variety of applications there is a need for efficient transmission of signals from a body location to an implanted device. Although this invention embraces various such applications, it will be illustrated primarily in the environment of the preferred embodiment, a pacemaker system.

Modern pacemaker systems have evolved greatly beyond the initial pacemakers which simply delivered a fixed rate of pacing pulses. Pacemakers are widely programmable to operate in different modes and to operate with different pacing parameters. Specifically, many pacemakers are rate responsive, meaning that they automatically sense the patient's demand, or need for rate variation, and adjust pacing rate accordingly. Pacemaker systems are also incorporating more sensor information relating to the patient's metabolic needs and cardiac history. The ability of the pacemaker to undertake additional diagnostic functions, and to accurately adapt pacemaker performance to metabolic needs, is dependent upon good sensor information.

As is well known, rate responsive or rate adaptive pacemakers may utilize any one of a number of different sensors for obtaining different physiologically based signals. Sensors that provide an indication of actual heart performance are coming into greater use. For example, sensors are used for measuring the pressure inside the patient's right ventricle, intramyocardial pressure, or myocardial contractility. Sensing pressure within the patient's heart is known to offer good potential for accurate determination of the patient's needs. See U.S. Pat. No. 5,353,800, assigned to Medtronic, Inc., which provides a discussion of the many different types of pressure sensors used in cardiac pacing systems.

As discussed in the prior art, the approach to measuring pressure changes within the heart has generally involved special leads adapted to carry a sensor which is located within the heart. Thus, a pressure sensor is located on the pacing lead close to the distal tip end, preferably positioned to maximize the sensor response. Such a lead requires extra wires throughout the length of the lead, for interconnection of the sensor signal to the pacemaker. Further, packaging a sensor in a lead tip, while maintaining the requisite minimal lead dimensions, presents considerable difficulty. Thus, it would be advantageous, both for newly implanted pacing systems and for replacement systems, to provide the pacemaker itself with one or more pressure sensors which receive pressure signals representative of cardiac movement, which signals are transmitted through a standard pacing lead and delivered to the pacemaker-mounted sensor. Such an arrangement, as presented by this invention, renders unnecessary any special lead construction, and by-passes the problems of fabricating a sensor on the lead and properly positioning the sensor within the heart. Further, for a patient requiring pacemaker, or pulse generator replacement, and already having a standard lead, it would clearly be advantageous to be able to replace the pacemaker with one which contains apparatus for reliably receiving a pressure signal transmitted through the implanted pacing lead.

There have been some prior art efforts to provide an implantable system with a catheter or lead which transmits a pressure signal from a body location such as the heart back to the control device, eg, the pacemaker. See, for example, U.S. Pat. Nos. 4,763,646 to Lekholm, and 5,353,800 to Pohndorf et al. These patents provide suggestions of transmitting pressure signals to the interior of a pacemaker can, but do not disclose efficient structure for achieving this. There thus remains a significant need in the implantable device art, and the pacemaker art in particular, for a system which provides for reliable and useful chronic transmission of signals such as pressure signals from an interior body location to the implanted device.

SUMMARY OF THE INVENTION

Accordingly, it is an object of this invention to provide an implantable medical device system, and particularly a pacemaker system, which achieves reliable and efficient transmission and coupling of pressure signals from a body location such as the heart to an implanted device such as a pacemaker, whereby accurate information can be obtained from such pressure signals.

The preferred embodiment of the present invention provides a pacing system which meets the object of utilizing a pressure sensor positioned in the implantable pacemaker, as contrasted to a system having a pressure sensor fabricated within the lead portion which is positioned in the patient's heart. The invention provides for utilizing relative pressure signals which are transmitted from the patient's heart through the lumen of a standard pacing lead, or any other pacing lead, which signals are communicated to a pressure sensor mounted either within the pacemaker connector block, or within the encapsulated pacemaker can. By this arrangement, the pacemaker-mounted sensor receives detectable pressure variations representative of heart movement, i.e., contraction and relaxation, and is able to transform such relative pressure signals into parameter signals for use in controlling a pacemaker operating variable such as pacing rate. The system may employ a second reference sensor, and may employ plural lead/catheters for transmitting the pressure signals to the implanted device.

Accordingly, there is provided a pacemaker system having a standard pacing lead with a central lumen, the pacing lead having a distal end which is inserted into the patient's heart, and a proximal end which is connected to the implanted pacemaker at the pacemaker connector block. The physical movement of the heart produces pressure changes in the outer wall or casing of the lead distal portion, which relative changes are transmitted to the interior lumen, and through the length of the lumen to the proximal end of the lead. In a first embodiment of the invention, a pressure transducer is positioned within the header, or connector block, at a distance from the lumen opening at the proximal end of the lead such that the relative pressure signals are effectively conveyed to the pressure sensor. Output signals from the pressure sensor are connected through an appropriate feed-through to the pacemaker, which uses the signals for any desired application, including pacing rate control and collection of diagnostic information. In another embodiment, the pressure sensor is mounted within the hermetically sealed pacemaker can, and the relative pressure variations transmitted through the lead lumen are further transmitted through a feed-through which interconnects the proximal lumen opening and the pressure sensor. The system of this invention is adaptable for providing a replacement pacemaker which can be implanted in any patient having a standard pacing lead or leads with a lumen, whereby the benefit of using pressure signals originating in or around the heart can be obtained.

DESCRIPTION OF THE PREFERRED EMBODIMENTS

Figure 1:
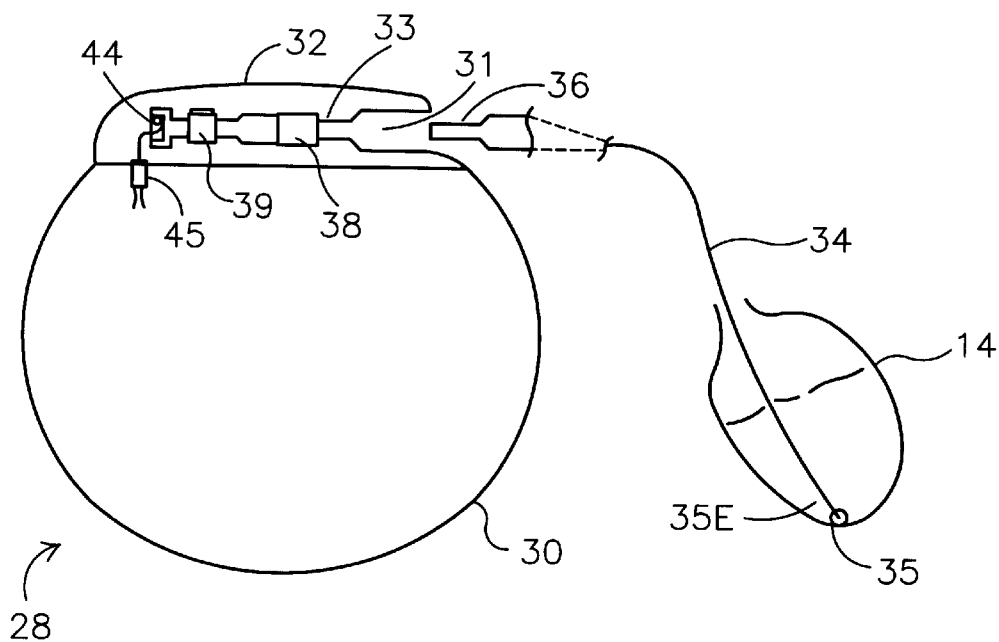
FIG. 1 is a diagrammatic perspective of a pacing system in accordance with this invention, having an implantable pacemaker interconnected with a pacing lead, the distal portion of the pacing lead being inserted in the patient's heart.

Referring now to FIG. 1, there is shown an illustration of a pacemaker system in accordance with this invention, comprising generally a pacemaker 28 and a lead 34. The pacemaker 28 has a can, or container 30 which houses the pacemaker electronics, and a header or connector portion 32, sometimes also referred to as the connector assembly. The can 30 provides a hermetically sealed container for protection of the pulse generator and other electronics contained therein from body fluids. The connector assembly 32 provides the mechanical and electrical connection between the pacemaker and the lead, in a well-known fashion. Reference is made to U.S. Pat. Nos. 5,188,078; 5,312,441; and 5,342,406 all incorporated herein by reference which disclose the structure of a connector assembly together with an implantable pulse generator or an implantable pacemaker—cardioverter—defibrillator.

Lead 34 is shown as having a tip electrode 35 at about its distal end 35E, which appropriately is inserted into the apex of the right ventricle. Although only a single unipolar lead is shown, it is to be understood that this invention can be practiced with a single chamber lead or dual chamber leads, and the leads can be unipolar or bipolar. The lead has a proximal end 36, which is inserted into opening or bore 31 formed in connector housing 33, suitably composed of uncolored, transparent epoxy. There is illustrated a first connector block 38 which is used for making electrical contact with a conductor which extends to the ring electrode of a bipolar lead, and second connector block 39 for making electrical contact with a conductor that extends to the tip electrode. The connector blocks may have a screw for fixation of the inserted lead, or a lead retainer comprising a spring contact. There is also illustrated a pressure transducer 44, located to receive pressure signals communicated through the lumen of lead 34, and a feed-through element 45 for feeding the electrical signals from sensor 44 through to the interior of the pacemaker. As used herein, the term standard pacing lead refers to one which has a central lumen, e.g., one through which a stylet may be inserted during the implantation procedure, and has conventional distal and proximal ends.

Figure 2:
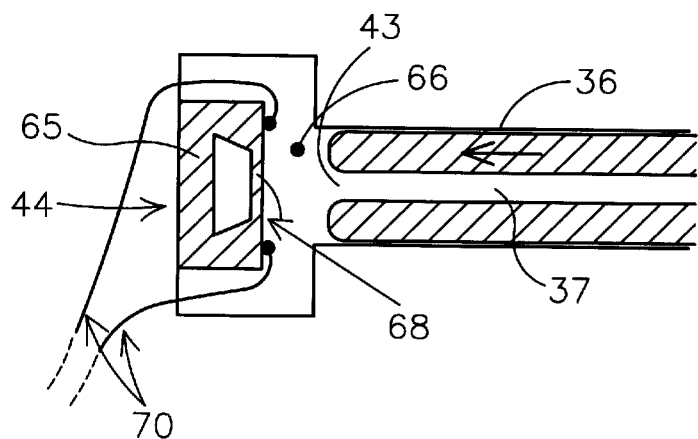
FIG. 2 is a detailed diagram representative of a first embodiment having a pressure transducer mounted within in a cavity within the header portion of the pacemaker.

Referring now to FIG. 2, there is illustrated the details of the proximal end 36 of the lead, and its placement relative to a pressure transducer 44. The lead has an inner lumen 37, typically centrally located within a coil which runs the length of the lead, the coil providing electrical interconnections between the proximal end and the distal electrode or electrodes. Lumen 37 opens at 43, the opening being a size to receive a stylet. Opening 43 opens into a cavity 66, provided in the header portion. A pressure sensor element 44 is mounted in close proximity to the lumen opening 43. In practice, it is important to make the cavity as small as possible, so as to have good transmission matching of the lumen to the cavity. The volume of this cavity, or chamber, adds to the volume of the lumen, such that the larger this cavity the smaller the available pressure change; the cavity volume is preferably significantly smaller than the volume of the lumen. For a lead with a lumen volume in the range of 110–140 mm$^3$, a cavity volume which is only 10% as large would be about 14 mm$^3$. The pressure sensor element is constructed from two layers, namely a silicon back plate 65 and a silicon diaphragm 68, which are sealed together. The cavity inside this construction is evacuated, to create an absolute pressure sensor. In this embodiment, the output of the sensor is taken by leads 70 and communicated by a feed-through element to the interior of the pacemaker can 30, as discussed in more detail in connection with FIG. 4.

Figure 3:
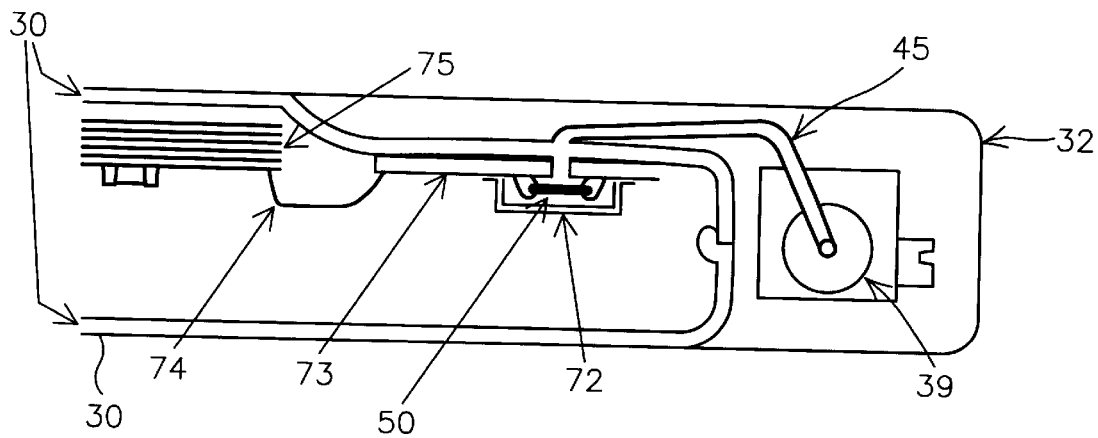
FIG. 3 is a detailed diagram illustrating another embodiment wherein the pressure signal from the lead is connected through a feed-through from the header portion to a pressure sensor mounted within the pacemaker can.

Referring now to FIG. 3, there is shown an alternate embodiment, wherein the pressure signal is transmitted from the lumen opening 43 through can 30 to transducer 50 by a feed-through capillary tube 45 which feeds through both the can 30 and a ceramic feed-through plate 73, as shown. The capillary tube material can be an isolator, e.g., a suitable plastic tube, or a metal tube for a combined electrical and pressure feed-through. The medium within the tube may be simply air, or it can be filled with a suitable gel which transmits the pressure signals. The end of feed-through tube 45 which is within the pacemaker can interfaces directly to the sensor element of sensor 50, which in turn is mounted within a cavity formed by the feed-through plate 73 and a sealed inner cover 72, as shown. The sealed inner cover provides protection against sensor membrane damage, and consequent leakage into the inside of the pacemaker. The volume within cover 72 is evacuated, to avoid any influence of the gas pressure within it due to temperature variation. The signal output of the sensor is connected through one or more wire 74 to a hybrid circuit illustrated at 75.

In a specific embodiment of a combined feed-through tube 45, a metal tube is utilized to provide both the capillary tube for transmitting the pressure signal and the electrical connection to the tip electrode. The metal tube must be shaped to connect properly to the terminal portion 39 and also interface with the opening 43 of the lumen. In this embodiment, the ceramic feed-through plate 73 contains a conductor (not shown) to pick up the electrical signal from the metal tube and couple it to the hybrid circuit.

Figure 4:
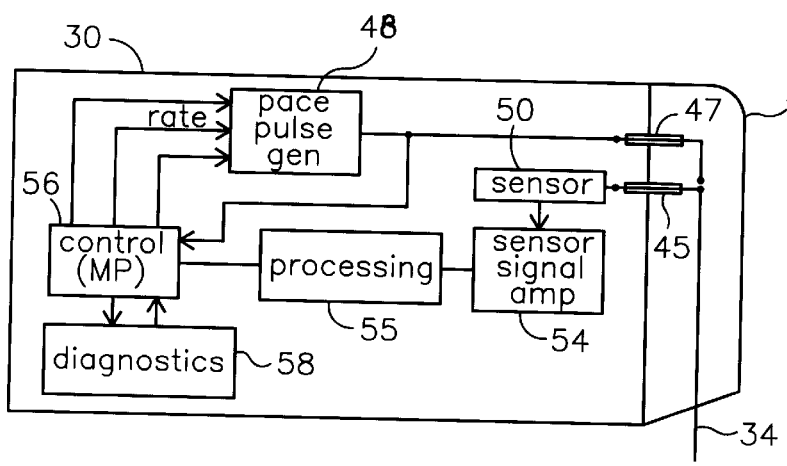
FIG. 4 is a block diagram illustrating the primary portions of the pacemaker in accordance with this invention, and the interconnection of the pacing lead to the pacemaker.

Referring now to FIG. 4, there is shown a diagram of the pacemaker portion of the pacing system of this invention. As indicated, the lead 34 has its proximal end connected to the pacemaker within the header section 32. A feed-through 47 is shown for connecting electrical signals between the lead and the inside of the pacemaker can 30. Also, a capillary feed-through 45 is shown for connecting pressure signals between the lead and a sensor 50 mounted internally to the pacemaker. It is to be understood that for the embodiment of FIG. 2, the feed-through 47 also carries the signals from the pressure sensor; while for the embodiment of FIG. 3 the feed-through 45 carries the pressure signals between the connector block and the inside of the pacemaker.

Figure 5:
FIG. 5 is a flow diagram representing the primary processing steps taken to utilize the pressure signal data obtained in accordance with this invention.

Whether the sensor is mounted within the header 32 or within the can 30, the sensor signals are connected to a sensor signal amplifier 54, and following processing circuitry 55 which, among other things, filters out the DC component (in the case of an absolute pressure sensor) and creates a suitable signal for storage and use by the microprocessor, as discussed further in connection with FIG. 5. These circuits may be part of a hybrid circuit, as illustrated at 75 in FIG. 3. The processed sensor signals are connected to a control block 56, indicated in the drawing of FIG. 4 as including a microprocessor. The microprocessor, in a known manner in the pacemaker art, generates a number of control signals for controlling pace pulse generator 48. One of these signals, indicated as rate, is derived in accordance with this invention from the processed pressure sensor signals. The output of the pace pulse generator is connected through feed-through 47 to the pacing lead. The output of the pace pulse generator is also connected back to the control circuit, such that the control circuit receives the information when a pace pulse has been delivered and also when a signal from the heart is transmitted from lead 34 back to the pacemaker. Also shown is a diagnostics block 58, suitably containing memory for storing diagnostic information, including information gained from the pressure sensor. This information can be used in further control of the pacemaker operation, or can be stored for readout to external apparatus, in a known manner.

It is to be noted that the invention as described does not require any special lead. Thus, any pacing lead which has a lumen running the length thereof, as is the case for a standard pacing lead adapted to receive a stylet, is applicable for use in this invention. Tests containing a pressure sensor of the type KPY43A have been conducted, where an IS-1-type lead has been inserted into a header, and pressure changes applied to the distal end of the lead. The pressure changes cause a compression of the lead tube, which causes a relative change of pressure in the lumen. Measurements have indicated that a 40 mm Hg pressure change at the distal end causes a pressure change in the lumen of approximately 0.4 mm Hg, as detected at the proximal end.

While the invention as disclosed can be used with a standard pacing lead, it is also applicable with leads which are modified to be more sensitive at specific points, and in particular at the distal end. The lead can be made more sensitive to pressure changes at the distal end, i.e., have a high pressure transfer characteristic, or can be modified to be more sensitive to conversion of bending pressure into relative pressure changes. Even though the pressure changes detected are relative, they exhibit a morphology which can be processed to provide significant information for use in a pacing environment. Indeed, in dog tests performed using the system of this invention, the recorded pressure signal clearly showed atrial contractions and ventricular contractions. Although the atrial contractions are represented by smaller peaks than the ventricular contractions, they can be separated, or windowed out, so that both P-wave and QRS information is available. Thus, the system of this invention, using either a standard pacing lead or one modified specially for conducting pressure signals from the heart, can be used in a dual chamber pacing context, and specifically for a VDD mode pacemaker. Thus, appropriate processing of the pressure signals can be performed so that ventricular pacing can be synchronized with respect to detected atrial contractions. The pressure signals may also contain other useful information concerning respiration, minute ventilation, etc.

Referring now to FIG. 5, there is shown a simplified block diagram illustrating the primary steps in electrical processing of the analog output from the sensor. At block 85, the analog signal is amplified, and then connected to block 86 for bandpass filtering which is adapted to the signals that the system is looking for. As noted above, the filtering may include filtering out the DC component in the case of an absolute pressure sensor, although this step need not be done in a system that uses relative pressure sensors. Next, at block 88, the filtered signal is captured by windowing and threshold detection. After this, the identified portions of the signal are converted into digital form and processed for the desired control purposes, e.g. for controlling the next ventricular and/or atrial pace pulses. Of course, for a dual chamber pacemaker, there may be two leads providing separate atrial and ventricular pressure signals. The processing step may suitably compare these respective signals to attain enhanced atrial and ventricular signals with minimal crosstalk. Alternately, in the VDD embodiment, the respective atrial and ventricular signals are separated out based upon windowing and comparative frequency or morphology characteristics of the signals.

It is to be noted that the invention as claimed is not limited by the applications to which the pressure data obtained by the system may be used, either in a pacemaker or other medical device environment. By way of example only, in the pacemaker environment, pressure data may be used to confirm evoked responses, or may be used in combination with an activity sensor to exclude false senses. The pressure signals may be combined with detected cardiac signals such as the QRS and T waves, for either control or diagnostic purposes. Likewise, EMI detection and rejection may be enhanced by utilizing the pressure signals.

I claim:

1. A pacemaker system having a pacemaker for delivering pacing pulses and a standard pacing lead for transmitting electrical signals between said pacemaker and a patient's heart, said lead having a distal end adapted to be placed in the patient's heart, a proximal end, and a lumen throughout its length suitable for transmitting pressure variations caused by heart activity, said lumen having a proximal opening at its proximal end, whereby pressure variations caused by said heart activity arise within said lumen and are transmitted to said proximal opening, said pacemaker comprising:
   a connector portion for receiving the proximal end of said lead;
   a pressure sensor which produces signals corresponding to said transmitted pressure variations;
   coupling means for coupling pressure variations between said lumen proximal opening and said pressure sensor, said coupling means having a cavity positioned to receive said pressure variations directly from said opening,
   mounting means for mounting said sensor in said cavity, and
   control means operatively connected to said pressure sensor for controlling pacemaker operation as a function of said transmitted pressure variations.

2. The pacemaker system as described in claim 1, wherein said pacemaker comprises a first portion containing a pulse generator and said control means, and wherein said pressure sensor is mounted in said first portion.

3. The pacemaker system as described in claim 2, comprising sealing means for sealing said first portion from entry of body fluids, and wherein sail coupling means comprises feed-through means for feeding said pressure variations from said proximal opening to said sensor.

4. The pacemaker system as described in claim 1, wherein said cavity has a size that provides an efficient match to receive said transmitted pressure variations.

5. The pacemaker system as described in claim 4, wherein said lumen has a first volume and said cavity has a second volume, and said second volume is about 10% of said first volume.

6. The pacemaker system as described in claim 1, wherein said pacemaker comprises a first sealed portion containing a pulse generator and said control means, first feed-through means for connecting electrical signals between said first portion and said connector portion, and second feed-through means for connecting said sensor signals to said control means.

7. The pacemaker as described in claim 6, comprising a cavity in said first portion, and wherein said mounting means and said sensor are placed in said cavity.

8. The pacemaker as described in claim 7, comprising second sealing means for sealing said cavity from the remainder of said first portion.

9. The pacemaker as described in claim 7, wherein said feed-through means has an opening into said cavity, and wherein said sensor is positioned proximal to said opening.

10. A pacemaker system having a pacemaker and a pacing lead connected with said pacemaker, said lead having a distal end for insertion into a patient's heart and a proximal end for connection to said pacemaker, said lead having a lumen substantially throughout its length suitable for transmitting pressure variations caused by heart movements, said lumen having a proximal opening to which said pressure variations are transmitted, said pacemaker having:
    a connector portion for connectedly receiving the proximal end of said lead,
    a pressure sensor which produces signals corresponding to pressure variations delivered thereto,
    coupling means matched to said lumen for coupling pressure variations received at said lumen proximal opening to said pressure sensor, and
    control means connected to receive signals from said pressure sensor for controlling pacemaker operation as a function of said relative pressure variations; and said lead comprising a portion at its distal end which is sensitive to pressure changes.

11. The pacemaker system as described in claim 10, wherein said coupling means comprises a cavity in said pacemaker having a volume which is small compared to the volume of said lumen, and wherein said sensor is mounted in said cavity.

12. The pacemaker system as described in claim 11, wherein said lead has a distal electrode for sensing patient heart signals and a conductor for conducting said heart signals to said lead proximal end, and wherein said coupling means further comprises means for coupling said heart signals from said lead proximal end to within said pacemaker.

13. An implantable medical system which obtains data representative of at least one body area or body function, said system comprising:
    a catheter having a distal end for placement so as to be impacted by activity of said body area or by said body function, a proximal end and a lumen extending between said ends, said lumen having a lumen volume, and
    a medical device having a connector portion which connectedly receives said proximal end; at least one sensor; a coupling portion which is at least partially in said connector portion for coupling signals from said lumen to said sensor, said coupling portion having a cavity having a volume no greater than about ten percent of said lumen volume, mounting means for mounting said at least one sensor in said cavity; and signal means for obtaining from said at least one sensor signals representative of said body area or body function.

14. The system as described in claim 13, wherein said medical device is a pacemaker, said signal means further comprising means to obtain signals representative of both atrial and ventricular contractions.

15. The system as described in claim 13, wherein said pacemaker has control means for operating in a VDD mode.

* * * * *